United States Patent

Yoshimura et al.

Patent Number: 5,811,408
Date of Patent: Sep. 22, 1998

[54] 2'-DEOXY-2'-(SUBSTITUTED OR UNSUBSTITUTED)METHYLIDENE-4'-THIONUCLEOSIDES

[75] Inventors: Yuichi Yoshimura, Kashima-gun; Akira Matsuda, Sapporo; Shinji Miura, Choshi; Takuma Sasaki, Kanazawa; Hiroshi Satoh, Choshi, all of Japan

[73] Assignee: Yamasa Corporation, Japan

[21] Appl. No.: 765,403

[22] PCT Filed: Jul. 12, 1995

[86] PCT No.: PCT/JP95/01385

§ 371 Date: Feb. 21, 1997

§ 102(e) Date: Feb. 21, 1997

[87] PCT Pub. No.: WO96/01834

PCT Pub. Date: Jan. 25, 1996

[30] Foreign Application Priority Data

Jul. 12, 1994 [JP] Japan ................. 6-182948

[51] Int. Cl.⁶ ............ C07H 19/207; C07H 19/10; C07H 19/73; C07H 19/173; A61K 31/70

[52] U.S. Cl. ............ 514/45; 514/46; 514/47; 514/48; 514/49; 514/50; 514/51; 514/261; 514/81; 514/86; 514/269; 536/26.7; 536/26.8; 536/27.6; 536/27.8; 536/27.81; 536/28.5; 536/28.53; 536/4.1; 544/264; 544/242

[58] Field of Search ............ 514/261, 269, 514/45, 46, 47, 48, 49, 50, 51, 81, 86; 536/26.7, 26.8, 27.6, 27.8, 27.81, 28.5, 28.53, 4.1; 544/242, 264

[56] References Cited

U.S. PATENT DOCUMENTS

| 3,585,189 | 6/1971 | Verheyden et al. ............ 536/27.4 |
| 5,026,835 | 6/1991 | Ueda et al. ............ 536/28.5 |
| 5,047,520 | 9/1991 | Matsuda et al. ............ 536/28.5 |
| 5,183,882 | 2/1993 | Sakata et al. ............ 514/49 |
| 5,206,244 | 4/1993 | Zahler et al. ............ 514/262 |
| 5,300,636 | 4/1994 | Matsuda et al. ............ 536/28.5 |
| 5,401,726 | 3/1995 | Ueda et al. ............ 514/49 |
| 5,412,089 | 5/1995 | Sakata et al. ............ 536/28.5 |
| 5,430,139 | 7/1995 | Matsuda et al. ............ 536/28.5 |
| 5,508,393 | 4/1996 | McCarthy et al. ............ 536/28.5 |
| 5,591,722 | 1/1997 | Montgomery et al. ............ 514/45 |
| 5,607,925 | 3/1997 | Matthews et al. ............ 514/45 |
| 5,616,702 | 4/1997 | Matthews et al. ............ 536/27.13 |
| 5,639,647 | 6/1997 | Usman et al. ............ 435/199 |

FOREIGN PATENT DOCUMENTS

| 0365849 | 5/1990 | European Pat. Off. . |
| 0372268 | 6/1990 | European Pat. Off. . |
| 9514523 | 10/1996 | Germany . |
| 2-160769 | 6/1990 | Japan . |
| 2-178272 | 7/1990 | Japan . |
| 5-310777 | 11/1993 | Japan . |
| 6-340531 | 12/1994 | Japan . |
| 9087295 | 3/1997 | Japan . |
| 9320825 | 10/1993 | WIPO . |
| 9601834 | 1/1996 | WIPO . |

OTHER PUBLICATIONS

Yoshimura et al. (I), "A Novel Synthesis of Antineoplastic 4'-Thionucleosides Using D-Glucose as a Chiral Synthon," *22nd Symposium on Nucleic Acid Chemistry, Nucleic Acids Symposium Series*, No. 34. Oxford University Press, Oxford, UK, originally disclosed Nov. 8–10, 1995 at Yokoyama, Japan.

Yoshimura et al. (II), "A Novel Synthesis of New Antineoplastics 2'-Deoxy-2'-substitued-4'-thiocytidines," *J. Organic Chem.*, 61(3), 822–823 (Feb. 9, 1996).

Yoshimura et al. (III), "A Novel Synthesis of 2'-Modified-2'-deoxy-4'-thiocytidines From D-Glucose," *J. Organic Chem.*, 62(10), 3140–3152 (May 16, 1997).

Shinji et al., "In Vitro and In Vivo Antitumor Activity of a Novel Nucleoside, 4'-Thio-2'-deoxy-2'-methylenecytidine," *Biol Pharm. Bull.*, 19(10), 1311–1315 (1996); *Chem. Abstr.*, 126(1), Abstr. No. 510m, p. 51 (Jan. 6, 1997); only Abstract supplied.

Takenuki et al., "Design, Synthesis and Antineoplastic Activity of 2'-Deoxy-2'-methylidenecytidine," *J. Medicinal Chem.*, 31(6), 1063–1064 (Jun. 1988).

Lin et al., "Synthesis and Anticancer and Antiviral Activities of Various 2'- and 3'-Methylidene-Substituted Nucleoside Analogues and Crystal Structure of 2'-Deoxy-2'-methylenecytidine Hydrochloride," *J. Medicinal Chem.*, 34(8), 2607–2615 (Aug. 1991).

*Primary Examiner*—Marian C. Knode
*Assistant Examiner*—L. Eric Crane
*Attorney, Agent, or Firm*—Wenderoth, Lind, Ponack, L.L.P.

[57] ABSTRACT

The present invention relates to 2'-deoxy-2'-(substituted or unsubstituted)methylidene-4'-thionucleosides having excellent antitumor activity, represented by formula [I]:

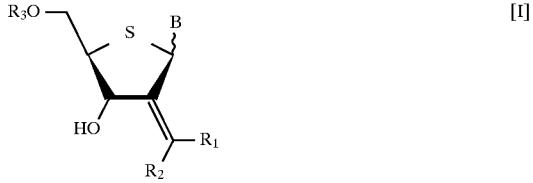

wherein B represents a pyrimidine or purine base, $R_1$ and $R_2$, which may be the same or different, represent hydrogen, a cyano group or alkyl group, and $R_3$ represents hydrogen or a phosphoric acid residue, and a method for producing the same, and a use of the same.

14 Claims, No Drawings

5,811,408

2'-DEOXY-2'-(SUBSTITUTED OR UNSUBSTITUTED)METHYLIDENE-4'-THIONUCLEOSIDES

This application is a 371 of PCT/JP95/01385, filed Jul. 12, 1995.

TECHNICAL FIELD

The present invention relates to 2'-deoxy-2'-(substituted or unsubstituted)methylidene-4'-thionucleosides, a process for producing the same, and a use of the same.

BACKGROUND ART

With respect to the synthesis or biological activity of 4'-thionucleosides, reports have been hitherto made by the group of the Roswell Memorial Research Institute and/or Purdue University (J. Org. Chem., 36, 108–110 (1971), J. Med. Chem., 17, 535–537 (1974), J. Med. Chem., 18, 784–787 (1975), J. Org. Chem., 41, 3831–3834 (1976), Nucleic Acid Chemistry, 1, 317–323 (1978)), the group of the Southern Research Institute (J. Med. Chem., 34, 2361–2366 (1991), Nucleosides & Nucleotides, 12, 841–846 (1993)), the group of the University of Birmingham (J. Chem. Soc. Chem. Commun., 741–742 (1991), J. Med. Chem., 34, 2782–2786 (1991)), the group of Okayama University (J. Chem. Soc. Chem. Commun., 1421–1422 (1991), Nucleic Acids Symposium Series, 27, 77–78 (1992), Nucleic Acids Symposium Series, 29, 37–39 (1993), Chemistry Letters, 255–256 (1993), The Pharmaceutical Society of Japan, Proceedings of the 113th Symposium, page 82 (1993)), the group of the University of Montpellier (Nucleosides & Nucleotides, 11, 1467–1479 (1992), Nucleosides & Nucleotides, 12, 847–852 (1993)) and the like.

In addition to the above-described reports, two patent applications, Japanese Laid-Open Patent Publication No. 500666/1993 (WO 91/04033) and WO 91/16333, were made by the Southern Research Institute, and four patent applications, Japanese Laid-Open Patent Publications Nos. 506661/1992 (WO 91/01326) and 505791/1993 (WO 91/04982), Japanese Laid-Open Patent Publication No. 170760/1993 and WO 94/05687, were made by the University of Birmingham and/or The Welcome Foundation, Limited.

Furthermore, the following reports have also been made by some groups other than the above-described groups:

J. Am. Chem. Soc., 86, 5658–5663 (1964),
J. Org. Chem., 33, 189–192 (1968),
Can. J. Chem., 56, 794–802 (1978),
Nucleosides & Nucleotides, 12, 139–147 (1993),
WO 92/06993, and
WO 92/06102.

The antitumor activity of 4'-thionucleosides reported in the above-mentioned reports is not necessarily satisfactory when the clinical use of 41-thionucleosides as antineoplastic agents is taken into consideration. Therefore, there is still a need for compounds having more excellent antitumor activity.

2'-Methylidene nucleosides such as 2'-deoxy-2'-methylidenecytidine (Japanese Laid-Open Patent Publications Nos. 230699/1988 and 256698/1990) and 2'-deoxy-2'-fluoro-methylidenecytidine (Japanese Laid-Open Patent Publication No. 178272/1990) have excellent biological activity for solid cancers, so that the progress in the development thereof is now attracting attention.

We therefore made various studies in the synthesis of 4'-thionucleosides having methylidene at the 2'-position of the sugar moiety thereof. As a result, it became apparent that the methods formerly reported were applicable to the synthesis of the ribo-, ara-, or 2'- and/or 3'-deoxy-compounds of 4'-thionucleosides, but not suggestive at all for the synthesis of 4'-thionucleosides having a substituent such as methylidene at the 2'-position of the sugar moiety thereof.

An object of the present invention is therefore to establish a novel method for synthesizing 4'-thionucleosides having methylidene at the 2'-position of the sugar moiety thereof, and, at the same time, to provide a novel and useful compound obtainable by this method.

DISCLOSURE OF THE INVENTION

We have made earnest studies in order to attain the above object, and, as a result, succeeded in obtaining 2'-deoxy-2'-(substituted or unsubstituted)methylidene-4'-thionucleosides represented by the below-described formula [I] by a novel synthetic method which we have found, and we have further confirmed that the compounds have excellent antitumor activity, thereby accomplishing the present invention.

Namely, the present invention relates to 2'-deoxy-2'-(substituted or unsubstituted)methylidene-4'-thionucleosides represented by the following formula [I]:

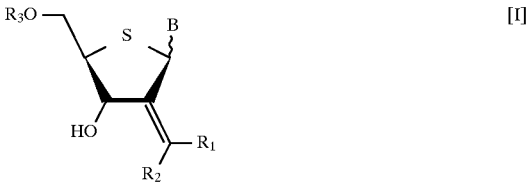

wherein B represents a pyrimidine or purine base, $R_1$ and $R_2$, which may be the same or different, represent hydrogen, a cyano group or alkyl group, and $R_3$ represents hydrogen or a phosphoric acid residue.

Further, the present invention relates to a pharmaceutical composition comprising a 2'-deoxy-2'-(substituted or unsubstituted)methylidene-4'-thionucleoside represented by the above formula [I] and a pharmaceutically acceptable carrier.

Furthermore, the present invention relates to a method for producing a 2'-deoxy-2'-(substituted or unsubstituted)-methylidene-4'-thionucleoside represented by the above formula [I], comprising the following 1st to 4th steps:

1st step a step in which sulfonyl group is introduced on the hydroxyl groups at the 2- and 5-positions of a compound represented by formula [II], and the resultant is then allowed to react with a sulfide to obtain a compound represented by formula [III]:

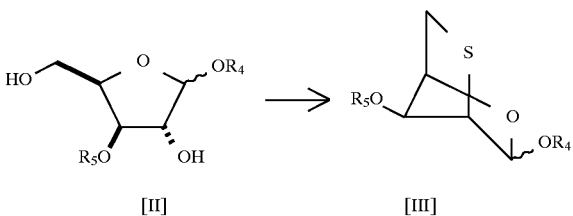

wherein $R_4$ represents an alkyl group or benzyl group, and $R_5$ represents a hydroxy protecting group;

2nd step a step in which the lactol ring of the compound represented by formula [III] is hydrolyzed, and the resultant is subjected to reduction to obtain a compound represented by formula [IV]:

[III] → [IV]

wherein $R_4$ and $R_5$ are as defined above; 3rd step a step in which the hydroxyl group at the 5-position of the compound represented by formula [IV] is protected, and the resulting compound is then subjected to oxidation reaction and Wittig reaction to obtain a compound represented by formula [V]:

[IV] → [V]

wherein $R_1$, $R_2$ and $R_5$ are as defined above, and $R_6$ represents a hydroxy protecting group; and 4th step a step in which the compound represented by formula [V] and a base represented by B are subjected to condensation reaction, the hydroxy protecting group in the sugar moiety is then removed, and, if desired, a phosphoric acid residue is introduced on the hydroxyl group at the 5'-position of the sugar moiety, thereby obtaining a compound represented by formula [I]:

[V] → [I]

wherein B, $R_1$, $R_2$, $R_3$, $R_5$ and $R_6$ are as defined above.

BEST MODE FOR CARRYING OUT THE INVENTION (1) Compound of the Invention

The compounds of the present invention are those represented by the above formula [I], in which B, $R_1$, $R_2$ and $R_3$ are as defined previously.

The pyrimidine base represented by B includes not only typical nucleic acid bases such as uracil, thymine and cytosine but also azapyrimidine bases (5-azapyrimidine, 6-azapyrimidine, etc.) and deazapyrimidine bases (3-deazapyrimidine, etc.). Further, those which are obtained by introducing one or more substituents [lower alkyl (1 to 5 carbon atoms), halogen, alkenyl, halogeno-alkenyl, alkynyl, amino, etc.] on any position of the above-described various bases are also useful. Examples of such a pyrimidine base having a substituent(s) include 5-ethyluracil, 5-propyluracil, 5-iodouracil, 5-fluorouracil, 5-vinyluracil, 5-bromovinyluracil, 5-chlorovinyluracil and 5-propynyluracil.

The purine base represented by B includes not only typical nucleic acid bases such as adenine, guanine and hypoxanthine but also azapurine bases (8-azapurine, 2-azapurine, etc.) and deazapurine bases (3-deazapurine, 7-deazapurine, etc.). Further, those which are obtained by introducing one or more substituents [lower alkyl (1 to 5 carbon atoms), halogen, amino, etc.] on any position of the above-described bases are also useful. Examples of such a purine base having a substituent(s) include 2,6-diaminopurine, 6-chloropurine, 6-chloro-2-aminopurine, 6-methoxypurine, 6-methoxy-2-aminopurine and 6-cyclopropylmethylamino-2-aminopurine.

Examples of the alkyl group represented by $R_1$ or $R_2$ include alkyls having 1 to 3 carbon atoms, such as methyl and ethyl.

Examples of the phosphoric acid residue represented by $R_3$ include ordinary monophosphoric, diphosphoric and triphosphoric acid residues.

The compound of the present invention may also be in the form of a salt, hydrate or solvate. Examples of such a salt include acid addition salts formed with an inorganic acid (hydrochloric acid, sulfuric acid, phosphoric acid, etc.) or with an organic acid (fumaric acid, tartaric acid, succinic acid, etc.), alkaline metal salts such as sodium, potassium and lithium salts, alkaline earth metal salts such as calcium and magnesium salts, and ammonium salt.

When such a salt is used for a pharmaceutical composition, it is preferable that the salt be pharmaceutically acceptable.

Examples of the hydrate or solvate include those in which 0.1 to 3.0 molecules of water or a solvent are combined with one molecule of a compound of the present invention or a salt thereof. Further, the compound of the present invention can also include various isomers thereof, such as alpha-anomer, beta-anomer and tautomer.

Specific examples of the compound of the present invention represented by formula [I] are, for example, the following compounds:

(1) Pyrimidine nucleosides:
B=cytosine, $R_1$=hydrogen, $R_2$=hydrogen, $R_3$=hydrogen;
B=cytosine, $R_1$=hydrogen, $R_2$=cyano, $R_3$=hydrogen;
B=cytosine, $R_1$=hydrogen, $R_2$=methyl, $R_3$=hydrogen;
B=cytosine, $R_1$=hydrogen, $R_2$=hydrogen, $R_3$=monophosphoric acid;
B=cytosine, $R_1$=hydrogen, $R_2$=cyano, $R_3$=monophosphoric acid;
B=cytosine, $R_1$=hydrogen, $R_2$=methyl, $R_3$=monophosphoric acid;
B=thymine, $R_1$=hydrogen, $R_2$=hydrogen, $R_3$=hydrogen;
B=thymine, $R_1$=hydrogen, $R_2$=cyano, $R_3$=hydrogen;
B=thymine, $R_1$=hydrogen, $R_2$=methyl, $R_3$=hydrogen;
B=thymine, $R_1$=hydrogen, $R_2$=hydrogen, $R_3$=monophosphoric acid;
B=thymine, $R_1$=hydrogen, $R_2$=cyano, $R_3$=monophosphoric acid;
B=thymine, $R_1$=hydrogen, $R_2$=methyl, $R_3$=monophosphoric acid;
B=uracil, $R_1$=hydrogen, $R_2$=hydrogen, $R_3$=hydrogen;
B=uracil, $R_1$=hydrogen, $R_2$=cyano, $R_3$=hydrogen;
B=uracil, $R_1$=hydrogen, $R_2$=methyl, $R_3$=hydrogen;
B=5-fluorouracil, $R_1$=hydrogen, $R_2$=hydrogen, $R_3$=hydrogen;

B=5-iodouracil, $R_1$=hydrogen, $R_2$=hydrogen, $R_3$=hydrogen;
B=5-bromeovinyluracil, $R_1$=hydrogen, $R_2$=hydrogen, $R_3$=hydrogen;
B=5-chlorovinyluracil, $R_1$=hydrogen, $R_2$=hydrogen, $R_3$=hydrogen;
B=5-propynyluracil, $R_1$=hydrogen, $R_2$=hydrogen, $R_3$=hydrogen;
B=5-azapyrimidine, $R_1$=hydrogen, $R_2$=hydrogen, $R_3$=hydrogen;
B=3-deazapyrimidine, $R_1$=hydrogen, $R_2$=hydrogen, $R_3$=hydrogen;

(2) Purine nucleosides:
B=adenine, $R_1$=hydrogen, $R_2$=hydrogen, $R_3$=hydrogen;
B=adenine, $R_1$=hydrogen, $R_2$=cyano, $R_3$=hydrogen;
B=adenine, $R_1$=hydrogen, $R_2$=methyl, $R_3$=hydrogen;
B=adenine, $R_1$=hydrogen, $R_2$=hydrogen, $R_3$=monophosphoric acid;
B=adenine, $R_1$=hydrogen, $R_2$=cyano, $R_3$=monophosphoric acid;
B=adenine, $R_1$=hydrogen, $R_2$=methyl, $R_3$=monophosphoric acid;
B=guanine, $R_1$=hydrogen, $R_2$=hydrogen, $R_3$=hydrogen;
B=guanine, $R_1$=hydrogen, $R_2$=cyano, $R_3$=hydrogen;
B=guanine, $R_1$=hydrogen, $R_2$=methyl, $R_3$=hydrogen;
B=guanine, $R_1$=hydrogen, $R_2$=hydrogen, $R_3$=monophosphoric acid;
B=guanine, $R_1$=hydrogen, $R_2$=cyano, $R_3$=monophosphoric acid;
B=guanine, $R_1$=hydrogen, $R_2$=methyl, $R_3$=monophosphoric acid;
B=hypoxanthine, $R_1$=hydrogen, $R_2$=hydrogen, $R_3$=hydrogen;
B=hypoxanthine, $R_1$=hydrogen, $R_2$=cyano, $R_3$=hydrogen;
B=hypoxanthine, $R_1$=hydrogen, $R_2$=methyl, $R_3$=hydrogen;
B=2,6-diaminopurine, $R_1$=hydrogen, $R_2$=hydrogen, $R_3$=hydrogen;
B=6-chloropurine, $R_1$=hydrogen, $R_2$=hydrogen, $R_3$=hydrogen;
B=6-chloro-2-aminopurine, $R_1$=hydrogen, $R_2$=hydrogen, $R_3$=hydrogen;
B=6-methoxypurine, $R_1$=hydrogen, $R_2$=hydrogen, $R_3$=hydrogen;
B=6-methoxy-2-aminopurine, $R_1$=hydrogen, $R_2$=hydrogen, $R_3$=hydrogen;
B=6-cyclopropylmethylamino-2-aminopurine, $R_1$=hydrogen, $R_2$=hydrogen, $R_3$=hydrogen;
B=8-azapurine, $R_1$=hydrogen, $R_2$=hydrogen, $R_3$=hydrogen;
B=3-deazapurine, $R_1$=hydrogen, $R_2$=hydrogen, $R_3$=hydrogen.

Of the above compounds of the present invention, those compounds which fulfill at least one of the following requirements (a) to (h) can be mentioned as preferred compounds:

(a) B is a pyrimidine base;
(b) B is cytosine;
(c) $R_1$ and $R_2$ are hydrogen;
(d) $R_3$ is hydrogen;
(e) $R_3$ is a monophosphoric acid residue;
(f) the compound is in the form of a salt;
(g) the compound is in the form of a hydrate; and
(h) the compound is a beta-anomer.

More preferable compounds are those which can fulfill the following requirement (i) or (j);

(i) B is cytosine, and $R_1$, $R_2$ and $R_3$ are hydrogen; and
(j) B is cytosine, $R_1$ and $R_2$ are hydrogen, and $R_3$ is a monophosphoric acid residue.

(2) Method for Producing the Compound of the Invention

A compound of the present invention can be produced via the following four steps, which will be explained hereinafter.

1st step

The 1st step of the present invention is a step in which sulfonyl group is introduced on the hydroxyl groups at the 2- and 5-positions of a compound represented by formula [II], and the resultant is then allowed to react with a sulfide to obtain a compound represented by formula [III]:

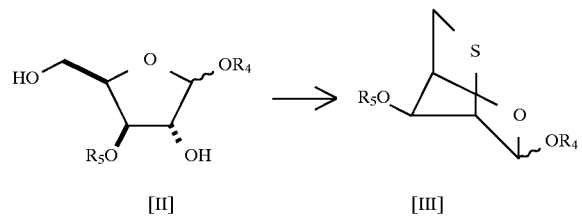

wherein $R_4$ represents an alkyl group or benzyl group, and $R_5$ represents a hydroxy protecting group.

The starting compound in the method of the present invention is a xylose derivative represented by formula [II] (hereinafter referred to often as the starting compound).

Examples of the alkyl group represented by $R_4$ include lower alkyl groups having approximately 1 to 3 carbon atoms, such as methyl and ethyl, and, examples of the benzyl group represented by $R_4$ include unsubstituted or substituted benzyl groups such as benzyl and methoxybenzyl.

As the hydroxy protecting group represented by $R_5$, any hydroxy protecting groups which are usually used, e.g. alkyl, silyl and acyl groups can be used. More specifically, as the alkyl group, the same ones as those described for $R_4$ are used. Further, as examples of the silyl group, t-butyldimethylsilyl, t-butyldiphenylsilyl and the like are used; and, as examples of the acyl group, acetyl, benzoyl, pivaloyl and the like are used.

Such a starting compound can be prepared by any known method (Tetrahedron, 37, 2379–2382 (1981), etc.).

A mesyl or tosyl group is used as the sulfonyl group which is introduced on the hydroxyl groups at the 2- and 5-positions of the compound represented by formula [II].

Mesylation or tosylation reaction can be carried out in accordance with a conventional method. For example, mesylation reaction can be carried out by allowing a starting compound to react, with stirring, with a mesyl halide (for instance, mesyl chloride) in an amount of 2 to 10 moles, preferably 2 to 4 moles per mole of the starting compound in the presence of a base such as triethylamine in an organic solvent such as methylene chloride, acetonitrile, dimethylformamide or pyridine (provided that when pyridine is used, it is not always needed to use the base such as triethylamine) at a temperature of 0° to 100° C. for approximately 0.5 to 5 hours. It is preferable to carry out the reaction under an atmosphere of inert gas such as argon or nitrogen.

Subsequently, the compound thus obtained is allowed to react with a sulfide, thereby obtaining a compound represented by formula [III].

There is no particular limitation on the sulfide used for the above reaction, and any sulfide can be used as long as it is a metal sulfide (preferably an alkaline metal sulfide) such as sodium sulfide or potassium sulfide.

The reaction can be carried out, with stirring, by using 1 to 20 moles of a sulfide per mole of the starting compound, in an organic solvent such as dimethylformamide or dimethyl sulfoxide, at a temperature of room temperature to 150° C. for approximately 0.5 to 5 hours under an atmosphere of inert gas such as argon or nitrogen, as needed.

The isolation and purification of the compound having formula [III] thus obtained may be conducted by selecting a suitable means out of the conventional means for the separation and purification of protected sugars. For example, after the reaction solution is partitioned with ethyl acetate and water, it is chromatographed on a silica gel column, eluting with an organic solvent mixture such as n-hexane/ethyl acetate, whereby compound [III] can be isolated and purified.

2nd step

The 2nd step of the present invention is a step in which the lactol ring of the compound represented by formula [III] is hydrolyzed, and the resultant is subjected to reduction to obtain a compound represented by formula [IV]:

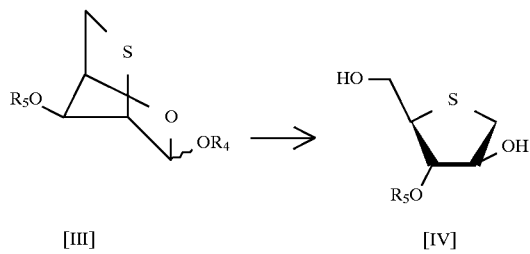

wherein $R_4$ and $R_5$ are as defined previously;

There is no particular limitation on the hydrolysis method, and any method can be employed as long as the lactol ring of the compound represented by formula [III] can be hydrolyzed by the method, a hydrolysis method using an acid catalyst being particularly preferred.

An inorganic acid such as hydrochloric acid or sulfuric acid, or an organic acid such as acetic acid or trifluoroacetic acid can be used as the acid catalyst.

The hydrolysis reaction can be carried out by allowing compound [III] to react, with stirring, at a temperature of room temperature to 100° C. for approximately 0.5 to 5 hours in the presence of the above-described acid catalyst in a water-soluble ether solvent such as tetrahydrofuran or dioxane.

Thereafter, the compound thus obtained is subjected to reduction reaction to obtain a compound represented by formula [IV].

A tetrahydroborate such as sodium tetrahydroborate (sodium boron hydride) or lithium tetrahydroborate can be used for the reduction reaction as a reducing agent.

The reduction reaction can be carried out by allowing the compound represented by formula [III] to react, with stirring, with a reducing agent in an amount of 0.2 to 10 moles per mole of compound [III] in an alcoholic solvent such as methanol, at a temperature of 0° to 100° C. for approximately 0.5 to 3 hours.

The isolation and purification of the compound having formula [IV] thus obtained may be conducted by properly applying a conventional means for the isolation and purification of protected sugars. For example, after the reaction is completed, the reaction solution is neutralized, and the organic solvent is evaporated; thereafter, the residue is extracted with chloroform, and the extract is subjected to silica gel column chromatography, whereby the desired compound can be isolated and purified.

3rd step:

The 3rd step of the present invention is a step in which the hydroxyl group at the 5-position of the compound represented by formula [IV] is protected, and the resulting compound is then subjected to oxidation reaction and Wittig reaction to obtain a compound represented by formula [V]:

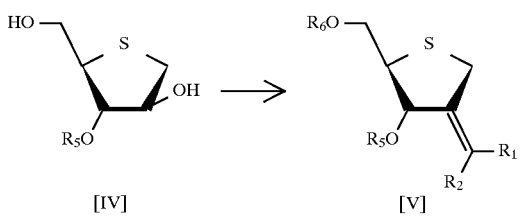

wherein $R_1$, $R_2$ and $R_5$ are as defined above, and $R_6$ represents a hydroxy protecting group.

There is no particular limitation on the hydroxy protecting group at the 5-position, and any hydroxy protecting group can be used as long as it is usually used as such. Examples of such a hydroxy protecting group include benzyl protective groups such as benzyl, methoxybenzyl and dimethoxybenzyl, silyl protective groups such as t-butyldimethylsilyl, t-butyldiphenylsilyl and triethylsilyl, ether protective groups such as methoxymethyl, methoxyethoxyethyl, tetrahydrofuran and tetrahydropyran, trityl protective groups such as trityl, monomethoxytrityl and dimethoxytrityl, and acyl groups such as acetyl, benzoyl and pivaloyl.

Further, it is also possible to remove the hydroxy protecting group at the 3-position and to protect the hydroxyl groups at the 3- and 5-positions at the same time by using a protective group capable of protecting two hydroxyl groups at the same time, such as teteraisopropyldisiloxyl.

The introduction of a protective group may be carried out in accordance with a method which is widely used for introducing the protective group used. For instance, when a silyl protective group is introduced, the protective group can be introduced by allowing the compound having formula [IV] to react with a silylating agent such as t-butyldiphenylsilyl chloride in an amount of 1 to 10 moles for 1 mole of compound [IV], with, if necessary, the addition of 1 to 5 moles of a base catalyst such as imidazole, in a solvent such as pyridine, picoline, dimethylaminopyridine, dimethylformamide, acetonitrile or methylene chloride, or a mixture thereof, at a temperature of −10° to 50° C. for 1 to 36 hours.

The compound thus obtained is subjected to oxidation reaction and Wittig reaction, thereby obtaining a compound represented by formula [V].

Examples of an oxidizing agent used for the oxidation reaction include chromium oxidizing agents such as a chromic anhydride-pyridine-acetic anhydride composite reagent, pyridium chlorochromate and pyridium dichromate; a high valency iodine oxidizing agent such as a Dess-Martin reagent; and dimethyl sulfoxide (DMSO) oxidizing agents using dimethyl sulfoxide in combination with acetic anhydride, oxalyl chloride or dicyclohexycarbodiimide.

In the case where the oxidation reaction is carried out by using, for example, dimethyl sulfoxide and acetic anhydride, it can be carried out by allowing the compound represented by formula [IV] to react, with stirring, with acetic anhydride in an amount of 2 to 500 moles, preferably 5 to 50 moles for 1 mole of compound [IV] in dimethyl sulfoxide, at a reaction temperature of 0° to 50° C. for approximately 1 to 24 hours under a stream of inert gas such as argon or nitrogen, if necessary.

There is no particular limitation on the ylide compound used for the Wittig reaction, and any ylide compound can be used as long as a methylene group having $R_1$ and $R_2$ can be introduced into compound [V]. Specifically, an unstable phosphorus ylide such as methylenetriphenylphosphorane, ethylenetriphenylphosphorane or propylenetriphenylphosphorane, or a stable phosphorus ylide such as ethoxycarbonylmethylenetriphenylphosphorane or cyanomethylenetriphenylphosphorane can be used.

Such a phosphorus ylide is prepared from a triphenylphosphonium salt (preferably, a bromide) having R1 and R2 obtained from triphenylphosphine, and a base such as butyl lithium, sodium hydride or potassium t-butoxide (preferably, butyl lithium) by a conventional method, and used for the Witting reaction.

The Wittig reaction can be carried out by allowing the compound represented by formula [IV] to react, with stirring, with a phosphorus ylide in an amount of 1 to 10 moles for 1 mole of compound [IV] in a solvent such as tetrahydrofuran, ether, dimethoxymethane or dimethyl sulfoxide, or a mixture thereof (preferably, in tetrahydrofuran) at a reaction temperature of −20° to 100° C. for approximately 1 to 24 hours under a stream of inert gas such as argon or nitrogen, if necessary.

The isolation and purification of the compound having formula [V] thus obtained may be conducted by selecting a proper means out of conventional means for the isolation and purification of protected sugars. For example, after the reaction is completed, the reaction solution is neutralized, and then extracted with ethyl acetate; after the solvent is evaporated, the residue is subjected to silica gel column chromatography, whereby the desired compound can be isolated and purified.

4th step

The 4th step of the present invention is a step in which the compound represented by formula [V] and a base represented by B are subjected to condensation reaction, the hydroxy protecting group in the sugar moiety is then removed, and, if desired, a phosphoric acid residue is introduced on the hydroxyl group at the 5'-position of the sugar moiety, thereby obtaining a compound represented by formula [I]:

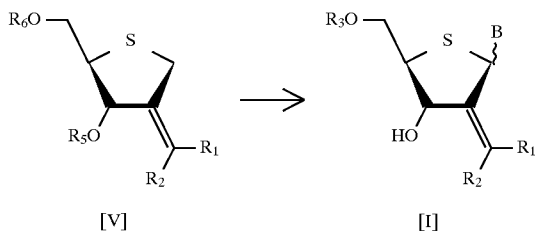

wherein B, $R_1$, $R_2$, $R_3$, $R_5$ and $R_6$ are as defined previously.

The condensation between the compound represented by formula [V] and the base represented by B can be carried out in the following manner: after the compound of formula [V] is oxidized into a sulfoxide by using a proper oxidizing agent, the sulfoxide is subjected to Pummerer-type reaction with a silylated base B in the presence of a Lewis acid catalyst.

Compound [V] can be oxidized into a sulfoxide in accordance with a conventional method. For instance, a sulfoxide can be obtained by allowing the compound represented by [V] to react with an oxidizing agent such as m-chloroperbenzoic acid or sodium metaperiodate in an amount of 0.5 to 5 moles for 1 mole of compound [V] in an organic solvent such as methylene chloride or an alcohol (e.g., methanol, etc.), at a temperature of −100° to 10° C. for approximately 10 minutes to 2 hours under a stream of inert gas such as argon or nitrogen, if necessary.

Examples of the Lewis acid catalyst used for the Pummerer-type reaction include trimethylsilyl trifluoromethanesulfonate (trimethylsilyl triflate), tin tetrachloride, titanium tetrachloride, zinc chloride, zinc iodide and boron trifluoride.

Glycosilation by means of the Pummerer-type reaction can be carried out by allowing 1 mole of the above-described sulfoxide to react with 1 to 10 moles of a base B which has been silylated by a conventional method and 0.1 to 10 moles of a Lewis acid in an organic solvent such as methylene chloride, chloroform, dichloroethane, acetonitrile or dimethylformamide, at a temperature of −50° to 100° C. for approximately 10 minutes to 2 hours under a stream of inert gas such as argon or nitrogen, if necessary.

Thereafter, the hydroxy protecting groups at the 3'-and 5'-positions of the sugar moiety of the nucleoside thus obtained are removed to obtain a compound whose $R_3$ is hydrogen.

The removal of the hydroxy protecting groups can be carried out by selecting a proper means, depending upon the protective group employed, out of conventional treatment methods such as acidic hydrolysis, alkaline hydrolysis, tetrabutylammonium fluoride treatment and catalytic hydrogenation. In the case where the protective group is a benzyl protective group, a deprotection method using boron trichloride is particularly preferred. This method can be carried out, for example, by reacting the nucleoside in an organic solvent such as methylene chloride, at a temperature of −100° C. to room temperature for approximately 0.5 to 24 hours under a stream of inert gas such as argon or nitrogen, if necessary.

The protective group represented by $R_5$ is not always needed to carry out the Pummerer-type reaction. It is therefore possible to remove the protective group before the Pummerer-type reaction is carried out, for instance, before the compound of formula [V] is oxidized into a sulfoxide.

Further, in the case where a compound whose $R_3$ is a phosphoric acid residue such as monophosphoric or diphosphoric acid residue is obtained, the desired compound of a free acid or salt type can be obtained by allowing the above-obtained compound whose R3 is hydrogen to react with a phosphorylating agent which is used for selectively phosphorylating the 5'-position of a nucleoside, such as phosphorus oxychloride or tetrachloropyrophosphoric acid.

The compound of the present invention thus obtained can be isolated and purified by the combination use of those methods which are usually used for the isolation and purification of nucleosides or nucleotides (for instance, recrystallization method, ion exchange column chromatography, adsorption column chromatography, etc.). The compound thus obtained can also be made into a salt-type compound, as needed.

(3) Use of the Compound of the Invention

The compounds of the present invention have remarkable proliferation inhibitory effects on various carcinoma cells (e.g., stomach adenocarcinoma, colon adenocarcinoma, pancreas carcinoma, small cell lung carcinoma, large cell lung carcinoma, lung squamous cell carcinoma, breast carcinoma, bladder carcinoma, osteosarcoma, esophagus carcinoma, melanoma, soft tissue sarcoma, leukemia, etc.), and useful for the therapy or prevention of the recurrence of a variety of human cancers such as lung cancer, cancers of alimentary system (cancers of the esophagus, stomach, vectum, colon, pancreas, etc.), breast cancer, cancers of urinary organs (cancers of the kidney, bladder, etc.), cancers of gynecological organs (cancers of the uterus, etc.), osteosarcoma, leukemia, melanoma and the like.

Any administration route such as oral, parenteral, rectal or topical administration can be adopted for administering the compound of the invention. The dose of the compound is properly determined depending upon the age, condition and body weight of the patient. The dose is selected, in general, from the range of 0.0001 to 10000 mg/kg of body weight per day, preferably from the range of 0.01 to 1000 mg/kg of body weight per day. The compound in such a amount is administered at one time, or divided into sub-doses and administered at several times.

When the compound of the present invention is formulated into a preparation, it is common to prepare the preparation as a composition containing a carrier, an excipient and other additives which are generally used for preparations. Examples of the carrier include solid carriers such as lactose, kaolin, saccharose, crystalline cellulose, corn starch, talc, agar, pectin, stearic acid, magnesium stearate, lecithin and sodium chloride, and liquid carriers such as glycerol, peanut oil, polyvinyl pyrrolidone, olive oil, ethanol, benzyl alcohol, propylene glycol and water.

The preparation can take any form. For instance, when a solid carrier is used, examples of the form of the preparation include tablet, powder, granule, capsule, suppository and troche; and when a liquid carrier is used, syrup, emulsion, soft gelatin capsule, cream, gel, paste, spray and injection.

EXAMPLES

The present invention will now be explained more specifically by referring to the following examples, though the present invention is not limited by these examples in any way.

Example 1

Synthesis of 2'-deoxy-2'-methylidene-4'-thiocytidine [formula [I], B=cytosine, $R_1$, $R_2$, $R_3$=H]

1) Synthesis of 2,5-anhydro-3-O-benzyl-1-O-methyl-2-thio-beta-D-arabinofuranose [formula [III], $R_4$=Me, $R_5$=Bn]

To 80 ml of a solution prepared by dissolving 6.93 g of 3-O-benzyl-1-O-methyl-beta-D-xylofuranose [formula [II], $R_4$=Me, $R_5$=Bn] in pyridine was added 6.33 ml of methane-sulfonylchloride with ice cooling, and the mixture was stirred at room temperature for 1 hour under a stream of argon. After the reaction was terminated by the addition of ice water, the solvent was evaporated. The residue was partitioned with ethyl acetate/water, and the organic layer was dried. After the solvent was evaporated, the residue was dissolved in 100 ml of dimethylformamide (DMF). To this solution was added 9.84 g of sodium sulfide, and the mixture was stirred at 100° C. for 1 hour under a stream or argon. After the solvent was evaporated, the residue was partitioned with ethyl acetate/water. The organic layer was further washed with water, and then dried. After the solvent was distilled off, the residue was purified by silica gel column chromatography. The fractions obtained by elution with 5–10% ethyl acetate/n-hexane were combined and concentrated, thereby obtaining 5.05 g (yield 73%) of the desired compound.

$^1$H—NMR (CDCl$_3$) δ7.36–7.29 (5 H, m, C$_6$H$_5$CH$_2$), 4.89 (1 H, s, H-1) , 4.62 (1H, d, C$_6$H$_5$CH$_2$, J=11.7 Hz), 4.52–4.48 (2 H, m, C$_6$H$_5$CH$_2$and H-3), 4.37–4.36 (1 H, m, H-4) 3.34 (4 H, s, OMe and H-2) , 3.04 (1 H, dd, H-5 a, J=10.3, 2.0 Hz), 2.77 (1 H, d d, H-5 b, J=10.3, 1.5 Hz)

2) Synthesis of 2,5-anhydro-3-O-benzyl-1-O-methyl-2-thio-alpha-D-arabinofuranose [formula [III], $R_4$=Me, $R_5$=Bn]

The same procedure as the above (1) was repeated by using 6.13 g of 3-O-benzyl-1-O-methyl-alpha-D-xylofuranose [formula [II], $R_4$=Me, $R_5$=Bn], thereby obtaining 4.75 g (yield 78%) of the desired compound.

$^1$H—NMR (CDCl$_3$) δ7.39–7.30 (5 H, m, C$_6$H$_5$CH$_2$), 5.13 (1 H, d, H-1, J=2.4 Hz), 4.66 (1 H, d, C$_6$H$_5$CH$_2$, J=11.7 Hz) 4.53 (1 H, d, C$_6$H$_5$CH$_2$), 4.36–4.35 (1 H, brm, H-4), 4.29 (1 H, t, H-3, J=2.4 Hz), 3.51 (1 H, t, H-2, J=2.4 Hz), 3.47 (3 H, s, OMe), 3.04 (1 H, dd, H-5 a, J=10.5, 2.2 Hz) , 2.95 (1 H, d d, H-5 b, J=10.5, 1.2 Hz)

3) Synthesis of 3-O-benzyl-1-deoxy-4-thio-D-arabino-furanose [formula [IV], $R_5$=Bn]

9.50 g of 2,5-anhydro-3-O-benzyl-1-O-methyl-2-thio-D-arabinofuranose (alpha:beta =1:1) was dissolved in 200 ml of tetrahydrofuran (THF). To this solution was added 100 ml of 4N HCl, and the mixture was stirred at room temperature for 1 hour. The reaction solution was neutralized with solid sodium hydrogencarbonate. After the insoluble matter was filtered off, THF was evaporated under reduced pressure. The resultant was extracted three times with chloroform, and the organic layer was dried. After the solvent was evaporated, the residue was dissolved in 150 ml of methanol. To this solution, a methanol solution containing 1.43 g of sodium borohydride was added dropwise with ice cooling. After the addition was completed, the mixture was stirred for 45 minutes with ice cooling. After the reaction solution was neutralized with acetic acid, the solvent was evaporated, and the residue was partitioned with chloroform/water. The aqueous layer was extracted twice with chloroform, and the organic layer was dried. After the solvent was evaporated, the residue was subjected to silica gel column chromatography. The fractions obtained by elution with 33–50% ethyl acetate/n-hexane were concentrated, thereby obtaining 8.18 g (yield 90%) of 3-O-benzyl-1-deoxy-4-thio-D-arabino-furanose.

$^1$H—NMR (CDCl$_3$-D$_2$O) δ7.38–7.27 (5 H, m, C$_6$H$_5$CH$_2$), 4.64 (2 H, S, C$_6$H$_5$CH$_2$) , 4.38 (1 H, d t, H-2, J=2.9, 4.4 Hz), 3.96 (1 H, t, H-3, J=2.9 Hz), 3.78 (1 H, dd, H-5 a, J=2.9, 11.7 Hz), 3.66 (1 H, d d, H-5 b, J=3.9, 11.7 Hz), 3.60 (1 H, dt, H-4, J=2.9, 3.9 Hz), 3.21 (1 H, d d, H-1 a, J=4.4, 11.2 Hz), 2.90 (1 H, dd, H-1 b, J=2.9, 11.2 Hz)

4) Synthesis of 3-O-benzyl-5-O-t-butyldiphenylsilyl-1-deoxy-2-methylene-4-thio-D-erythropentofuranose [formula [V], $R_1$=$R_2$=H, $R_5$=Bn, $R_6$=t-Bu(Ph)$_2$Si]

1.11 g of 3-O-benzyl-1-deoxy-4-thio-D-arabinofuranose and 330 mg of imidazole were dissolved in 30 ml of DMF. To this solution was added 1.26 ml of t-butyldiphenylsilyl chloride (TBDPSCl) with ice cooling, and the mixture was stirred at 0° C. overnight under a stream of argon. Water was added to the mixture, and the resulting mixture was stirred at room temperature for a while. The solvent was then evaporated, and the residue was partitioned with ethyl acetate/water. The organic layer was further washed with water, and then dried. The solvent was evaporated, and the residue was purified by silica gel column chromatography. The fractions obtained by elution with 2%–4%–10% ethyl acetate/n-hexane were concentrated, thereby obtaining 1.92 g (yield 86%) of a 5-silylated compound.

1.79 g of this 5-silylated compound was dissolved in 20 ml of DMSO. To this solution was added 10 ml of acetic anhydride, and the mixture was stirred at room temperature overnight. This solution was diluted with water, and the resulting solution was then extracted three times with ether. The organic layer was washed three times with water, partitioned twice with a saturated sodium hydrogencarbonate solution, and then dried. After the solvent was evaporated, the residue was co-evaporated three times with toluene, and dissolved in 20 ml of THF. This solution was added dropwise to a solution of methylenetrimethylphosphorane(prepared from 3.3 equivalents of methyltriphenylphosphonoium bromide and 3 equivalents of butyl lithium in 20 ml of THF), and the mixture was stirred at 0° C. for 2 hours and at room temperature overnight under a stream of argon. The mixture was then neutralized with 1N ammonium chloride solution, and extracted with ethyl acetate. The organic layer was dried. After the solvent was evaporated under reduced pressure, the residue was purified by silica gel column chromatography. The fractions obtained by elution with 2% ethyl acetate/n-hexane were concentrated, thereby obtaining 1.01 g (yield 57%) of the desired compound.

$^1$H—NMR (CDCl$_3$) δ7.60–7.27 (15 H, m, C$_6$H$_5$) 5.13, 4.94 (each 1 H, s, 2-CH$_2$), 4.64 (1 H, d, C$_6$H$_5$CH$_2$, J=12.7 Hz), 4.44 (1 H, d, C$_6$H$_5$CH$_2$), 4.35 (1 H, s, H-3) , 3.62–3.31 (4 H, m, H-4, 5, 1 a), 3.21 (1 H, d, H-1 b, J=12.7 Hz), 0.99 (9 H, s, t Bu)

5) Synthesis of 2'-deoxy-2'-methylidene-4'-thiocytidine [formula [I], B=cytosine, R$_1$, R$_2$, R$_3$═H]

1.37 g of 3-O-benzyl-5-O-t-butyldiphenylsilyl-1-deoxy-2-methylene-4-thio-D-erythropentofuranose was dissolved in 20 ml of methylene chloride. To this solution was added dropwise 5.78 ml of 1M trichloroborane at −78° C. under a stream of argon, and the mixture was stirred at −78° C. for 1 hour. 5 ml of pyridine and 10 ml of methanol were added to the mixture, and the resulting mixture was stirred at −78° C. for a further 30 minutes. Thereafter, the temperature of the mixture was raised to room temperature, and the solvent was evaporated. The residue was co-evaporated three times with methanol, and then dissolved in ethyl acetate. The mixture was partitioned with water and 0.5N hydrochloric acid (twice), and with saturated sodium hydrogencarbonate and a saturated saline solution. The organic layer was dried. After the solvent was evaporated, the residue was purified by silica gel column chromatography, thereby obtaining 750 mg (yield 70%) of a debenzylated compound.

523 mg of this debenzylated compound was dissolved in 15 ml of methylene chloride, and the solution was cooled to −78° C. under a stream of argon. To this solution was added dropwise a solution prepared by dissolving 271 mg of 80% m-chloroperbenzoic acid in methylene chloride. After the mixture was stirred for 30 minutes, a saturated sodium hydrogencarbonate solution was added to the mixture to terminate the reaction, and the temperature of the mixture was raised to room temperature. The mixture was then extracted with chloroform, and the organic layer was dried. The solvent was evaporated, and the residue was dissolved in 10 ml of acetonitrile. To this solution were added silylated N$^4$-acetylcytosine (prepared by reacting 644 mg of N$^4$-acetylcytosine with a catalytic amount of ammonium sulfate for 5 hours in hexamethyldisilazane under reflux) and 0.56 ml of trimethylsilyl triflate, and the mixture was stirred at 0° C. for 30 minutes. A saturated sodium hydrogencarbonate solution was added to the mixture, and the insoluble matter was removed by filtration on Celite. The resultant was extracted three times with chloroform, and the organic layer was dried. The filtrate was concentrated under reduced pressure, and the residue was purified by silica gel column chromatography. The fractions obtained by elution with 1% methanol/chloroform were combined and concentrated, thereby obtaining 200 mg (yield 23%) of the desired compound.

238 mg of the compound obtained was dissolved in 10 ml of THF. To this solution was added 0.78 ml of 1M tetrabutylammonium fluoride, and the mixture was stirred at room temperature for 15 minutes. The solvent was evaporated, and the residue was purified by silica gel column chromatography. The fractions obtained by elution with 4–8% methanol/chloroform were combined and concentrated. The compound obtained was dissolved in 5 ml of methanol. To this solution was added 5 ml of conc. ammonia water, and the mixture was stirred at room temperature overnight. The solvent was evaporated, and the residue was purified by ODS chromatography. Further, the alpha- and beta-anomers were separated by HPLC, whereby 34 mg (34%) of the purified alpha-anomer and 13 mg (13%) of the purified beta-anomer were respectively obtained. α-Anomer:

$^1$H—NMR (DMSO-d$_6$) δ7.61 (1 H, H-6, J=7.2 Hz), 7.24 (2 H. bs, NH$_2$), 6.64 (1 H, s, H a -1') 5.85 (1 H, b s, H-5), 5.79 (1 H, d, 3'-OH, J=5.9 Hz), 5.32 (1 H, s, 2'-CH$_2$ a), 4.98 (1 H, t, 5'-OH, J=5.4 Hz), 4.80 (1 H s, 2'-CH$_2$ b) 4.28 (1 H, b t, H-3', J=7 8 Hz). 3.81 (1 H, ddd, H-5'a, J=3.9, 10.7 Hz), 3.45 (1 H, d d d, H-5'b, J=7.8 Hz) 3.37 (1 H, bt, H-4') β-Anomer:

$^1$H—NMR (DMSO-d$_6$) δ7.57 (1 H, d, H-6, J=7.3 Hz), 7.24, 7.20 (total 2 H, bs, NH$_2$), 6.66 (1 H, s, H-1'), 5.79 (1 H, bd, H-5), 5.62 (1 H, S, 2'-CH$_2$ a), 5.32 (1 H, d, 3'-OH, J=4.9 Hz), 5.07 (1 H, t, 5'-OH, J=5.4 Hz), 4.92 (1 H, s, 2'-CH$_2$b) , 4.49 (1 H, b t, H-3', J=4.9 Hz), 3.60 (1 H, ddd, H-5'a, J=6.4, 11.2 Hz), 3.49 (1 H, ddd, H-5'b, J=6.4 Hz), 3.12 (1 H, d t, H-4').

Example 2

Synthesis of 2'-deoxy-2'-methylidene-4'-thio-5-fluorocytidine [formula [I], B=5-fluorocytosine, R$_1$, R$_2$, R$_3$═H]

The procedure of Example 1 was repeated except that the N$^4$-acetylcytosine used in (5) of Example 1 was replaced by 5-fluorocytosine, thereby obtaining the title compound. α-Anomer:

$^1$H—NMR (DMSO-d$_6$) δ7.88 (2 H, bd, H-6, NH$_2$, J=7.3 Hz), 7.61 (1 H, b s, NH$_2$), 6.55 (1 H, d, H-1', J=2.0 Hz), 5.79 (1 H, d, 3'-OH, J=5.9 Hz), 5.37 (1 H, s, 2'-CH$_2$a), 4.99 (1 H, t, 5'-OH, J=5.1 Hz) 4.95 (1 H, s, 2'-CH$_2$ b) 4.33 (1 H, m, H-3'), 3.72 (1 H, m, H-4'), 3 47~3.42 (2 H, m, H-5'a, H-5'b) β-Anomer:

$^1$H—NMR (DMSO-d$_6$) δ7.86 (1 H, d, H-6, J=6.8 Hz), 7.62 (2 H, bs, NH$_2$), 6.60 (1 H, s, H-1'), 5.64 (1 H, d, 3'-OH, J=4.9 Hz), 5.32 (1 H, S, 2'-CH$_2$ a), 5.16 (1 H, t, 5'-OH, J=5.4 Hz), 5.01 (1 H, S, 2'-CH$_2$ b) , 4.53 (1 H, t, H-3', J$_{3',4'}$=4.4 Hz), 3.68~3.56 (2 H, ddx2, H-5'a, H-5b, J$_{4',5'a}$=J$_{4',5'b}$=5.9 Hz, J$_{5'a,\ 5'b}$=11.7 Hz), 3.19 (1 H, d t, H-4', J$_{4',5'a}$=J$_{4',5'b}$=5.9 Hz, J$_{4',3'}$=4.9 Hz).

Example 3

Synthesis of 2'-deoxy-2'-methylidene-4'-thio-5-methyluridine [formula [I], B=thymine, R$_1$, R$_2$, R$_3$═H]

The procedure of Example 1 was repeated except that the N$^4$-acetylcytosine used in (5) of Example 1 was replaced by thymine, thereby obtaining the title compound. α-Anomer:

$^1$H—NMR (DMSO-d$_6$) δ11.38 (1 H, bs, NH), 7.45 (1 H, d, H-6, NH$_2$, J=1.0 Hz), 6.53 (1 H, s, H-1'), 5.84 (1 H, d, 3'-OH, J=5.9 Hz) , 5.36 (1 H, t, 2'-CH$_2$ a, J=2.0 Hz) , 5.02 (1 H, t, 5'-OH, J=5.4 Hz), 4.94 (1 H, t, 2'-CH$_2$ b, J=2.0 H z), 4.27 (1 H, m, H-3'), 3.50~3.40 (2 H, m, H-5'a, H-5'b), 1.79 (3 H, d, CH$_3$, J=1.0 Hz) β-Anomer:

$^1$H—NMR (DMSO-d$_6$) δ7.45 (1 H, d, H-6, J=1.0 Hz), 6.59 (1 H, s, H-1'), 5.69 (1 H, d, 3'-OH, J=4.4 Hz), 5.36 (1 H, s, 2'-CH$_2$ a), 5.20 (1 H, b s, 5'-OH), 5.03 (1 H, s, 2'-CH$_2$ b) 4.57 (1 H, d, H-3', J$_{3',4'}$=3.9 Hz) , 3.68~3.56 (2 H, ddx 2, H-5'a, H-5'b, J$_{4',5'a}$=5.9 Hz, J$_{4',\ 5'b}$ 6.4 Hz, J$_{5'a,\ 5'b}$=11.5 Hz), 3.21 (1 H, d t, H-4'J$_{4',5'a}$=5.9 Hz, J$_{4',5'b}$=6.4 Hz, J$_{4',3'}$=3.9 Hz), 1.79 (3 H, d, CH$_3$ , J=1.0 Hz).

Example 4

Synthesis of 7-(2-deoxy-2-C-methylidene-4-thio-D-erythropentofuranosyl) adenine [formula [I], B=adenine, R$_1$, R$_2$, R$_3$═H]

1) Synthesis of 1-deoxy-2-methylene-3,5-O-tetraisopropyldisiloxan-1,3-diyl-4-thio-D-erythropentofuranose [formula [V], R$_1$═R$_2$═H, R$_5$═R$_6$═TIPDS]

5.7 g of 5-O-t-butyldiphenylsilyl-1-deoxy-2-methylene-4-thio-D-erythropentofuranose obtained by removing the benzyl group from 3-O-benzyl-5-O-t-butyldiphenylsilyl-1-deoxy-2-methylene-4-thio-D-erythropentofuranose which had been prepared in (4) of Example 1 was dissolved in 80 ml of THF. To this solution was added 29.6 ml of 1M tetrabutylammonium fluoride, and the mixture was stirred at room temperature for 30 minutes. After the solvent was evaporated, the residue was purified by silica gel column chromatography, thereby obtaining 2.4 g of a desilylated compound.

The whole amount of this desilylated compound was dissolved in 75 ml of pyridine. To this solution was added dropwise 7.1 ml of dichlorotetraisopropyl disiloxane (TIPDSCl) at 0° C. under a stream of argon. The temperature of the mixture was raised to room temperature, and the mixture was stirred overnight. After the reaction was terminated by the addition of water, the solvent was evaporated. To the residue was added ethyl acetate, and the resulting suspension was partitioned with 1N hydro-chloric acid, a saturated sodium hydrogencarbonate solution, water (three times) and a saturated saline solution. After the organic layer was dried, the solvent was evaporated. The residue was purified by silica gel column chromatography, thereby obtaining 4.3 g (yield 75%) of the desired compound.

$^1$H—NMR (CDCl$_3$) δ5.20 (1 H, d d, CH$_2$ a, J=2.4, 1.5 Hz), 5.00 (1 H, dd, CH$_2$ b, J=1.0, 2.4 Hz) 4.58 (1 H, bd, H-3, J=9.3 Hz), 4.10 (1 H, dd, H-5 a, J=2.9, 9.3 Hz), 3.89 (1 H, dd, H5 b, J=3.4, 9.3 Hz), 3.55 (1 H, dd, H1 a, J=1.5, 13.7 Hz), 3.42 (1 H, dd, H1 b, J=1.0, 13.7 Hz), 3.10 (1 H, d t, H4, J=3.2, 9.3 Hz), 1.07 (28 H, m, i-Pr)

2) Synthesis of 7-(2-deoxy-2-C-methylidene-4-thio-D-erythropentofuranosyl)adenine [formula [I], B=adenine, R$_1$, R$_2$, R$_3$=H]

4.3 g of 1-deoxy-2-methylene-3,5-O-tetraisopropyl-disiloxan-1,3-diyl-4-thio-D-erythropentofuranose was dissolved in 120 ml of methylene chloride, and the mixture was cooled to −78° C. under a stream of argon. To this was added dropwise a solution prepared by dissolving 2.39 g of 80% m-chloroperbenzoic acid in methylene chloride. After the mixture was stirred for 30 minutes, the reaction was terminated by the addition of a saturated sodium hydrogencarbonate solution. The temperature of the mixture was raised to room temperature, and the mixture was then extracted with chloroform. The organic layer was dried, and the solvent was evaporated, thereby obtaining 4.6 g of a sulfoxide.

236 mg of the sulfoxide obtained was dissolved in 10 ml of dichloroethane. To this were added silylated adenine (prepared by reacting 239 mg of adenine with a catalytic amount of ammonium sulfate overnight in hexamethyldisilazane under reflux) and 140 microliters of trimethylsilyl triflate at 0° C. under a stream of argon, and the mixture was stirred at 0° C. for 3 hours. A saturated sodium hydrogen-carbonate solution was added to this solution, and the insoluble matter was removed by filtration on Celite. The reaction solution was diluted with chloroform, and then partitioned with water (three times) and a saturated saline solution. The organic layer was dried, and the solvent was evaporated. The residue was purified by silica gel column chromatography, thereby obtaining 111.3 mg (yield 36.5%) of the desired compound.

105 mg of the compound obtained was dissolved in 10 ml of THF, and to this solution was added 0.6 ml of 1M tetrabutylammonium fluoride. The mixture was stirred at room temperature for 25 minutes. The solvent was evaporated, and the residue was purified by silica gel column chromatography. The fractions obtained by elution with 25% methanol/chloroform were combined, and the solvent was evaporated. The residue was subjected to HPLC to separate and purify the alpha- and beta-anomers, whereby 16.2 mg (29%) uf the alpha-anomer and 14.1 mg (25%) of the beta-anomer were respectively obtained. α-Anomer:

$^1$H—NMR (DMSO-d$_6$) δ8.65 (1 H, S, H-8) 8.21 (1 H, S, H-2), 7.03 (2 H, bs, NH$_2$), 6.89 (1 H, s, H-1'), 5.79 (1 H, bd, 3'-OH, J=5.4 Hz), 5.32 (1 H, b s, CH$_2$ a), 5.23 (1 H, b t, 5'-OH, J=5.13 Hz), 5.18 (1 H, bs, CH$_2$ b), 4.57 (1 H, b S, H-3'), 3.80 (1 H, m, H-5 a), 3.69 (1H, m, H-5 b), 3.23 (1 H, m, H-4) UV (λmax) 275 nm (methanol) β-Anomer:

$^1$H—NMR (DMSO-d$_6$) δ8.48 (1 H, s, H-8), 8.22 (1 H, s, H-2), 6.93 (2 H, bs, NH$_2$), 6.90 (1 H, s, H-1'), 5.94 (1 H, bd, 3'-OH, J=6.4 Hz), 5.43 (1 H, b s, CH$_2$ a), 5.08 (1 H, b t, 5'-OH, J=5.13 Hz), 4.88 (1 H, b s, CH$_2$ b) , 4.43 (1 H, b t, H-3', J-6.59 Hz), 3.82 (1 H, m, H-5 a) 3.50 (2 H, m, H-4, 5 b) UV (λmax) : 275 nm (methanol)

Test Example 1

Proliferation Inhibitory Activity on Cultured Cells (in vitro test)

Method

Cells in the logarithmic growth phase were suspended in a medium for inoculation, and seeded into each well of a 96-well plate so that the number of the cells would be $3 \times 10^3/180$ microliters/well. To each well was added 20 microliters of a sample solution or water, and incubation was carried out at 37° C. for 72 hours. After incubation, 25 microliters of an MTT solution (2 mg/ml, prepared in PBS) was added, and incubation was further conducted at 37° C. for 4 hours. The medium was removed, and the MTT-formazane formed was dissolved in 200 microliters of dimethyl sulfoxide. The absorbance at 540 nm of this solution was measured by a microplate reader. The proliferation inhibitory rate obtained by calculation was plotted on a graph paper against the concentration of the sample. Then, the 50% inhibitory concentration (IC$_{50}$) was determined for evaluation of the antitumor effect.

Results

The results of the test carried out by using the compound of the present invention (the beta-anomer of 2'-deoxy-2'-methylidene-4'-thiocytidine synthesized in Example 1) are shown in Table 1.

TABLE 1

| Cell Strain | Origin | IC$_{50}$ (μg/ml) |
| --- | --- | --- |
| NUGC-4 | Stomach adenocarcinoma | 0.60 |
| KKLS | Stomach adenocarcinoma | 0.77 |
| Colo320DM | Colon adenocarcinoma | 0.060 |
| HCT-15 | Colon adenocarcinoma | 0.65 |
| Mia-PaCa-2 | Pancreas carcinoma | 2.4 |
| PC-10 | Lung squamous cell carcinoma | 1.5 |
| Lu-65 | Large cell lung carcinoma | 0.075 |
| QG-90 | Small cell lung carcinoma | 0.32 |
| QG-96 | Small cell lung carcinoma | 0.5 |
| MCF-7 | Breast carcinoma | 0.3 |
| KK-47 | Bladder carcinoma | 0.38 |
| HOS | Osteosarcoma | 0.45 |
| MG-63 | Osteosarcoma | 0.53 |
| HEp-2 | Esophagus carcinoma | 4.1 |
| A375 | Melanoma | 0.25 |
| SK-Mel-28 | Melanoma | 0.092 |
| HT1080 | Soft tissue sarcoma | 0.21 |

Test Example 2

Antitumor Activity in mice bearing P388 leukemia (in vivo test)

Method

DBA/2 mice were intraperitoneally inoculated with murine P388 leukemia cells. On day 0, ascites was collected from the DBA/2 mice, and P388 leukemia cells were intraperitoneally implanted into BDF1 mice so that the number of the cells would be $1 \times 10^6$/mouse. A sample was dissolved in dimethyl sulfoxide, and this sample solution was intraperitoneally administered to the mice once a day. The antitumor effect was evaluated by comparing the survival time of the administered group with that of the control group.

Results

The results of the test carried out by using the compound of the present invention (the beta-anomer of 2'-deoxy-2'-methylidene-4'-thiocytidine synthesized in Example 1) are shown in Table 2.

TABLE 2

| Sample | Dose (mg/kg) | Schedule | MST[a] (days) | T/C (%) |
|---|---|---|---|---|
| Control (DMSO) | — | Day 1, 2, 5, 6 | 9.0 | 100 |
| Compound of the Invention | 10 | Day 1, 2, 5, 6 | 12.0 | 133 |

[a]MST: Median survival time

Test Example 3
Antitumor Activity in Mice Implanted with S-180 Cells (in vivo test)
Method ICR mice were intraperitoneally inoculated with murine S-180 cells. On day 0, ascites was collected from the ICR mice, and Sarcoma 180 cells were subcutaneously implanted into ICR mice so that the number of the cells would be $5 \times 10^6$/mouse. A sample was suspended in Macrogol-400/Tween 80 (6:0.8) so that the concentration thereof would be 10 times the concentration at the time of the administration thereof. Thereafter, the suspension was diluted to 1/10 with physiological saline, and injected once a day into the caudal vein of the mice on days 1–5, and on days 7–10. The antitumor effect (inhibitory rate) was evaluated by measuring the weight of the tumor removed on day 35.

Results

The results of the test carried out by using the compound of the present invention (the beta-anomer of 2'-deoxy-2'-methylidene-4'-thiocytidine synthesized in Example 1) are shown in Table 3.

TABLE 3

| Sample | Dose (mg/kg/day) | Weight of Tumor[a] | Inhibitory Rate (%) |
|---|---|---|---|
| Control | — | 8.70 ± 1.31 | — |
| Compound of the Invention | 100 | 0.80 ± 0.24 | 90.8 |
|  | 20 | 6.39 ± 1.07 | 26.6 |

[a]mean value ± SE

Preparation Example 1: Tablet

| Compound of the invention | 30.0 mg |
|---|---|
| Cellulose fine powder | 25.0 mg |
| Lactose | 39.5 mg |
| Starch | 40.0 mg |
| Talc | 5.0 mg |
| Magnesium stearate | 0.5 mg |

A tablet preparation having the above formulation is prepared by a conventional method.

Preparation Example 2: Capsule

| Compound of the invention | 30.0 mg |
|---|---|
| Lactose | 40.0 mg |
| Starch | 15.0 mg |
| Talc | 5.0 mg |

A capsule preparation having the above formulation is prepared by a conventional method.

Preparation Example 3: Injection

| Compound of the invention | 30.0 mg |
|---|---|
| Glucose | 100.0 mg |

The above components are dissolved in purified water or injections, thereby preparing an injection.

INDUSTRIAL APPLICABILITY

The compounds of the present invention have excellent antitumor effect, and are thus expected to be developed into antineoplastic agents.

We claim:

1. A 2'-deoxy-2'-(substituted or unsubstituted)-methylidene-4'-thionucleoside represented by formula (I):

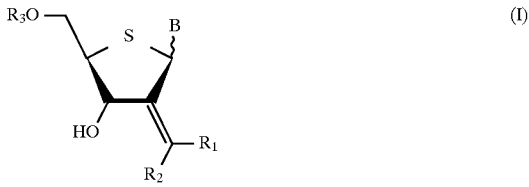

wherein B represents a pyrimidine or purine base, $R_1$ and $R_2$, which may be the same or different, represent hydrogen, a cyano group or alkyl group, and $R_3$ represents hydrogen or a phosphoric acid residue.

2. The compound according to claim 1, wherein B is a pyrimidine base.

3. The compound according to claim 1, wherein B is cytosine.

4. The compound according to claim 1, which is a beta-anomer.

5. The compound according to claim 1, wherein $R_1$ and $R_2$ are hydrogen.

6. The compound according to claim 1, wherein $R_3$ is hydrogen.

7. The compound according to claim 1, wherein $R_3$ is a phosphoric acid residue.

8. The compound according to claim 1, wherein B is cytosine, and $R_1$ and $R_2$ are hydrogen.

9. The compound according to claim 1, wherein B is cytosine, and $R_1$, $R_2$ and $R_3$ are hydrogen.

10. The compound according to claim 1, wherein B is cytosine, $R_1$ and $R_2$ are hydrogen, and $R_3$ is a phosphoric acid residue.

11. A pharmaceutical composition comprising a 2'-deoxy-2'-(substituted or unsubstituted)methylidene-4'-thionucleoside as set forth in any one of claim 1, and a pharmaceutically acceptable carrier.

12. A method of treating tumors which comprises administering to a patient having a tumor, the pharmaceutical composition according to claim 11 wherein the tumor is selected from the group consisting of stomach adenocarcinoma, colon adenocarcinoma, carcinoma of the pancreas, lung squamous cell carcinoma, large cell lung carcinoma, small cell lung carcinoma, breast carcinoma, bladder carcinoma, osteosarcoma, carcinoma of the esophagus, melanoma, and soft tissue sarcoma.

13. A method for producing a 2'-deoxy-2'- (substituted or unsubstituted) methylidene-4'-thionucleoside represented by formula (I):

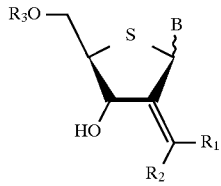

(I)

wherein B represents a pyrimidine or purine base, $R_1$ and $R_2$, which may be the same or different, represent hydrogen, a cyano group or alkyl group, and $R_3$ represents hydrogen or a phosphoric acid residue, comprising the following 1st to 4th steps:

1st step a step in which sulfonyl group is introduced on the hydroxyl groups at the 2- and 5-positions of a compound represented by formula (II), and the resultant is then allowed to react with a sulfide to obtain a compound represented by formula (III):

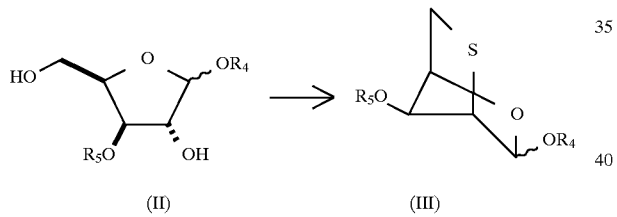

(II)          (III)

wherein $R_4$ represents an alkyl group or benzyl group, and $R_5$ represents a hydroxy protecting group;

2nd step a step in which the lactol ring of the compound represented by formula (III) is hydrolyzed, and the resultant is subjected to reduction to obtain a compound represented by formula (IV):

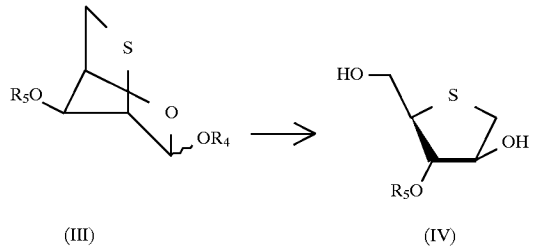

(III)          (IV)

wherein $R_4$ and $R_5$ are as defined above;

3rd step a step in which the hydroxyl group at the 5-position of the compound represented by formula (IV) is protected, and the resulting compound is then subjected to oxidation reaction and Wittig reaction to obtain a compound represented by formula (V):

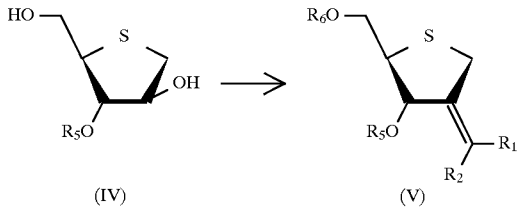

(IV)          (V)

wherein $R_1$, $R_2$ and $R_5$ are as defined above, and $R_6$ represents a hydroxy protecting group; and 4th step a step in which the compound represented by formula (V) and a base represented by B are subjected to condensation reaction, the hydroxy protecting group in the sugar moiety is then removed, and, optionally, a phosphoric acid residue is introduced by the hydroxyl group at the 5'-position of the sugar moiety, thereby obtaining a compound represented by formula (I):

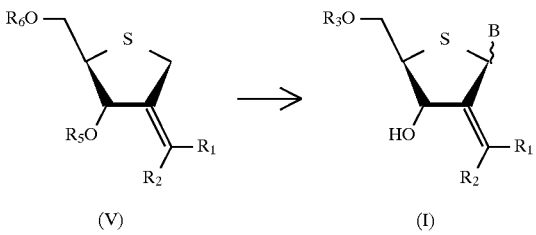

(V)          (I)

wherein B, $R_1$, $R_2$, $R_3$, $R_5$ and $R_6$ are as defined above.

14. A method of treating leukemia which comprises administering to a patient having leukemia the pharmaceutical composition according to claim 11.

* * * * *